United States Patent [19]

Evans

[11] Patent Number: 4,677,116
[45] Date of Patent: Jun. 30, 1987

[54] ANTIHYPERTENSIVE CHROMAN DERIVATIVES

[75] Inventor: John M. Evans, Roydon, England

[73] Assignee: Beecham Group p.l.c., England

[21] Appl. No.: 660,501

[22] Filed: Oct. 12, 1984

[30] Foreign Application Priority Data

Oct. 13, 1983 [GB] United Kingdom ............... 8327411
Mar. 7, 1984 [GB] United Kingdom ............... 8405955

[51] Int. Cl.[4] ..................... A61K 31/35; C07D 311/02
[52] U.S. Cl. .................................. 514/456; 549/404; 549/345
[58] Field of Search ............... 549/404, 405; 514/456

[56] References Cited

U.S. PATENT DOCUMENTS 3,103,520  9/1963  Zaugg et al. .............. 549/405
4,446,113  5/1984  Evans et al. .............. 546/196
4,568,692  2/1986  Evans ....................... 549/404
4,571,406  2/1986  Evans et al. .............. 514/456

FOREIGN PATENT DOCUMENTS 0001428  4/1979  European Pat. Off. ........... 514/456
0035868  9/1981  European Pat. Off. .
0095316 11/1983  European Pat. Off. .

OTHER PUBLICATIONS

Lap et al., Aust. J. Chem. 1979, 32 pp. 619–636.
Chem. Abst. vol. 77, 88182j (1972).

Primary Examiner—Nicky Chan
Attorney, Agent, or Firm—Jacobs & Jacobs

[57] ABSTRACT

Compounds of formula (I)

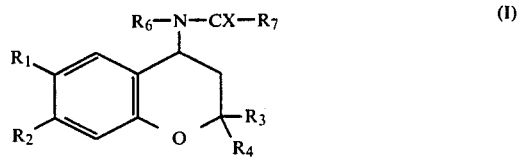

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkylthiocarbonyl, $C_{1-6}$ alkoxythiocarbonyl, $C_{1-6}$ alkylthiocarbonyloxy, $C_{1-6}$ alkylthiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together with the carbon atom to which they are attached are $C_{2-5}$ polymethylene;
$R_6$ is hydrogen or $C_{1-6}$ alkyl;
$R_7$ is hydrogen or $C_{1-6}$ alkyl optionally substituted by hydroxy, $C_{1-6}$ alkoxy, $C_{1-6}$ alkoxycarbonyl or carboxy, or $C_{1-2}$ alkyl substituted by halogen, or $C_{2-6}$ alkenyl;
X is oxygen or sulphur; or, when one or the other of $R_1$ and $R_2$ is an amino or an amino-containing group, a pharmaceutically acceptable salt thereof, processes for their preparation and their use in the treatment of hypertension.

10 Claims, No Drawings

ANTIHYPERTENSIVE CHROMAN DERIVATIVES

The present invention relates to novel chromans having pharmacological activity, to a process for preparing them, to pharmaceutical compositions containing them, and to their use in the treatment of mammals.

U.S. Pat. Nos. 4,110,347 and 4,119,643 and 4,251,537 and European Patent Publications Nos. 28 064 and 28 449 disclose classes of chromans that are described as having blood pressure lowering activity or anti-hypertensive activity.

A further class of chromans, has now been discovered which have been found to have blood pressure lowering activity.

Accordingly, the present invention provides a compound of formula (I):

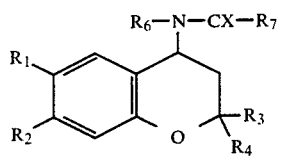

(I)

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkylthiocarbonyl, $C_{1-6}$ alkoxythiocarbonyl, $C_{1-6}$ alkylthiocarbonyloxy, $C_{1-6}$ alkylthiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)-NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl; one of $R_3$ and $R_4$ is hydrogen or $C_{1-4}$ alkyl and the other is $C_{1-4}$ alkyl or $R_3$ and $R_4$ together with the carbon atom to which they are attached are $C_{2-5}$ polymethylene;

$R_6$ is hydrogen or $C_{1-6}$ alkyl;

$R_7$ is hydrogen or $C_{1-6}$ alkyl optionally substituted by hydroxy, $C_{1-6}$ alkoxy, $C_{1-6}$ alkoxycarbonyl or carboxy, or $C_{1-2}$ alkyl substituted by halogen, or $C_{2-6}$ alkenyl;

X is oxygen or sulphur; or, when one or the other of $R_1$ and $R_2$ is an amino or an amino-containing group, a pharmaceutically acceptable salt thereof.

When one of $R_1$ and $R_2$ is hydrogen, the other is preferably selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro or cyano. In particular, when one of $R_1$ and $R_2$ is hydrogen, the other is preferably nitro or cyano.

When one of $R_1$ and $R_2$ is hydrogen, it is preferred that $R_2$ is hydrogen.

When one of $R_1$ and $R_2$ is nitro, cyano or $C_{1-3}$ alkylcarbonyl the other is preferably amino optionally substituted by one or two $C_{1-6}$ alkyl or by $C_{2-7}$ alkanoyl. In particular, when one of $R_1$ and $R_2$ is nitro, cyano or $C_{1-3}$ alkylcarbonyl, the other is amino, methylamino, diethylamino or acetylamino. Most preferably, one of $R_1$ and $R_2$ is nitro or cyano, especially cyano, and the other is amino.

When one of $R_1$ and $R_2$ is nitro, cyano or $C_{1-3}$ alkylcarbonyl, it is preferred that $R_1$ is nitro, cyano or $C_{1-3}$ alkylcarbonyl.

The alkyl groups or alkyl moieties of alkyl-containing groups for $R_1$ or $R_2$ are, preferably, methyl or ethyl.

Preferably, $R_3$ and $R_4$ are both $C_{1-4}$ alkyl. In particular, they are both methyl or ethyl, preferably both methyl.

Examples of $R_6$ include hydrogen, methyl, ethyl, n- or iso-propyl. Preferably, $R_6$ is hydrogen or methyl, especially hydrogen.

Examples of $R_7$, when $C_{1-6}$ alkyl, include methyl, ethyl and n- and iso-propyl. Preferably $R_7$, when $C_{1-6}$ alkyl, is methyl.

Examples of $R_7$, when $C_{1-6}$ alkyl substituted by hydroxy, include methyl or ethyl terminally substituted by hydroxy.

A sub-class of $R_7$, when $C_{1-6}$ alkyl substituted by $C_{1-6}$ alkoxy, is $C_{1-6}$ alkyl substituted by methoxy or ethoxy. Examples thereof include methyl or ethyl terminally substituted by methoxy or ethoxy.

A sub-class of $R_7$, when $C_{1-6}$ alkyl substituted by $C_{1-6}$ alkoxycarbonyl, is $C_{1-6}$ alkyl substituted by methoxycarbonyl or ethoxycarbonyl. Examples thereof include methyl or ethyl terminally substituted by methoxycarbonyl or ethoxycarboxy.

Examples of $R_7$, when $C_{1-6}$ alkyl substituted by carboxy, include methyl or ethyl terminally substituted by carboxy.

A sub-class of $R_7$, when $C_{1-2}$ alkyl substituted by halogen, is methyl or ethyl terminally substituted by chloro or bromo, in particular by chloro.

Examples of $R_7$, when $C_{2-6}$ alkenoyl, include vinyl, prop-1-enyl, prop-2-enyl, 1-methylinyl, but-1-enyl, but-2-enyl, but-3-enyl, 1-methylenepropyl, or 1-methylprop-2-enyl, in both their E and Z forms where stereoisomerism exists.

Examples of a pharmaceutically acceptable salt of a compound of formula (I), when one or the other of $R_1$ and $R_2$ is an amino or an amino-containing group, include the hydrochloride and hydrobromide salts.

The present invention also provides a process for preparing a compound of formula (I), which comprises acylating a compound of formula (II):

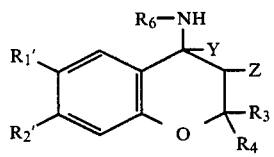

(II)

wherein $R_1'$ and $R_2'$ are $R_1$ and $R_2$, as hereinbefore defined, or a group or atom convertible thereto, $R_3$, $R_4$ and $R_6$ are as hereinbefore defined; Y and Z are both hydrogen or together form a bond with an acylating agent of formula (III):

(III)

wherein $R_7$ is as hereinbefore defined and $L_1$ is a leaving group; and thereafter in the case where $R_1'$ or $R_2'$ is a group or atom convertible into $R_1$ or $R_2$, converting the group or atom into $R_1$ or $R_2$; optionally converting $R_1$ or $R_2$ in the resulting compound into another $R_1$ or $R_2$; in the case where X and Y together form a bond, reducing the Y-Z; bond optionally thiating the $R_6$—N—CO—$R_7$ group in the resulting compound of formula (I) to give another compound of formula (I) wherein X is sulphur; and, when one or the other of $R_1$ and $R_2$ in the resulting compound of formula (I) is amino or an amino-containing group, optionally forming a pharmaceutically acceptable salt.

The leaving group ($L_1$) is a group that is displaceable by a primary or secondary amino nucleophile. Examples of such a group include $C_{2-9}$ acyloxy, such as mesyloxy, tosyloxy, triflate and $C_{1-4}$ alkylcarbonyloxy, and halogen, such as chloro and bromo. When the leaving group ($L_1$) is either of these examples, the acylating agent of formula (III) is either an acid anhydride or an acid halide. When it is acid anhydride, it may be a mixed or simple anhydride. If it is a mixed anhydride, it may be prepared in situ from a carboxylic acid and an acid halide.

When the acylating agent of formula (III) is an acid anhydride, the acylation of the compound of formula (II) is, preferably, carried out using the anhydride as the solvent in the presence of an acid acceptor, such as sodium acetate.

When the acylating agent of formula (III) is an acid halide, the acylation of the compound of formula (II) is, preferably, carried out in an aqueous medium, such as chloroform/water, in the presence of an acid acceptor, such as triethylamine, trimethylamine, pyridine, picoline or calcium, potassium or sodium carbonate.

Conversions of an aromatic group into $R_1$ or $R_2$, as hereinbefore defined, are generally known in the art of aromatic chemistry. For example, it is preferred when carrying out the acylation of a compound of formula (II), first to protect any unsubstituted terminal amine, that may be present for $R_1$ or $R_2$, such as amino aminosulphinyl, aminosulphonyl or aminocarbonyl, and afterwards to convert the protected amino moiety into the required terminal amine. Examples of protecting agents include acyl groups, such as acetyl, which may be added and removed conventionally. If it is desired to protect a terminal amino moiety in the presence of a cyano group then a more appropriate method is to use a trifluoroacetyl protecting group which may be removed by mild hydrolysis or to use a benzyloxycarbonyl or a p-nitrobenzyloxycarbonyl protecting group which may be removed by mild catalytic hydrogenolysis.

If the optional thiation reaction is to be carried out in order to obtain a compound of formula (I), wherein one or the other of $R_1$ and $R_2$ is a carbonyl-containing group and X is sulphur, it is preferred to use in the acylation reaction the corresponding compound of formula (II), wherein $R_1'$ or $R_2'$ is a protected carbonyl-containing group, and after thiation to convert the protected carbonyl-containing group into the required carbonyl-containing group for $R_1$ or $R_2$. Without such protection, the additional carbonyl group may give rise to a competing side-reaction. Examples of preferred carbonyl protecting groups include ketalising agents, which may be added and removed in conventional manner.

Examples of an optional conversion of $R_1$ or $R_2$ in the resulting compound of formula (I) into another $R_1$ or $R_2$, as defined hereinbefore, include the optional conversion of an α-hydroxethyl group into acetyl by oxidation, the optional conversion of a chloro atom into an amino group by amination, the optional conversion of an amino group into an amino group substituted by one or two $C_{1-6}$ alkyl or by $C_{2-7}$ alkanoyl, or the optional conversion of a hydrogen atom into a nitro group by nitration.

The reduction of a Y-Z bond may be carried out by conventional catalytic hydrogenation using Palladium on Charcoal.

The optional thiation of the $R_6$—N—CO—$R_7$ group in a compound of formula (I) to give another compound of formula I, wherein X is sulphur, is, preferably, carried out with conventional thiation agents, such as hydrogen sulphide, phosporous pentasulphide and Lawesson's reagent (p-methoxyphenylthiophosphine sulphide dimer). The use of hydrogen sulphide and phosporous pentasulphide may lead to side-reactions and, therefore, the use of Lawesson's reagent is preferred.

The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is preferably carried out under reflux in a dry solvent, such as toluene or methylene chloride.

The optional formation of a pharmaceutically acceptable salt, when one or the other of $R_1$ and $R_2$ in the resulting compound of formula (I) is amino or an amino-containing group, may be carried out conventionally.

It will be appreciated that the invention further provides a process for the preparation of a compound of formula (I) which process comprises the reduction of a compound of formula (IV):

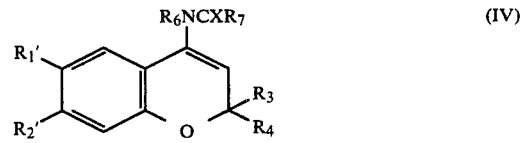

(IV)

wherein the variable groups are as hereinbefore defined; and thereafter in the case when $R_1'$ or $R_2'$ is a group or atom convertible into $R_1$ or $R_2$, converting the group or atom into $R_1$ or $R_2$; optionally converting $R_1$ or $R_2$ in the resulting compound of formula (I) into another $R_1$ or $R_2$; optionally thiating an $R_6$NHCX$R_7$ group wherein X is oxygen to give a corresponding compound of formula (I) wherein X is oxygen; and, when $R_1$ and/or $R_2$ is amino or an amino containing group, optionally forming a pharmaceutically acceptable salt.

Compounds of formula (II) wherein Y and Z are both hydrogen may be prepared by reduction of compounds of formula (I) wherein Y and Z form a bond.

Compounds of formula (II) wherein Y and Z form a bond may be prepared by the dehydration of a compound of formula (V):

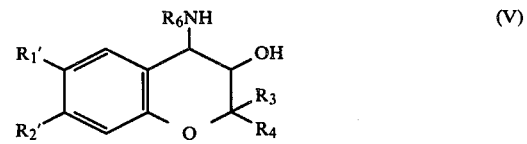

(V)

wherein the $R_6$NH and OH moieties are trans.

The dehydration may be carried out in accordance with conventional dehydration procedures, for example using a dehydrating agent, for example sodium hydride in an inert solvent, for example dry tetrahydrofuran at reflux temperatures.

A compound of formula (V) may be prepared by reacting a compound of formula (VI):

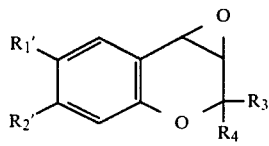
(VI)

wherein $R_1'$, $R_2'$, $R_3$ and $R_4$ are as hereinbefore defined, with a compound of formula (VII):

$R_6NH_2$ (VII)

or a salt thereof, wherein $R_6$ is as hereinbefore defined.

The reaction is normally carried out in a solvent, such as a $C_{1-4}$ alcohol, in particular methanol, ethanol or propanol at an ambient or an elevated temperature, for example 12° to 100° C. The reaction proceeds particularly smoothly if carried out in ethanol under reflux.

The resulting compound of formula (V) may be removed from the reaction mixture by removal of the solvent, for example, by evaporation under reduced pressure. Any epoxide impurity may be removed conventionally, for example by chromatography.

A compound of formula (VI) may be prepared, preferably in situ, by reacting a compound of formula (VIII):

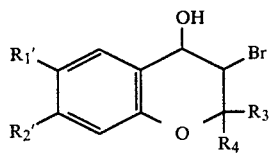
(VIII)

wherein $R_1'$, $R_2'$, $R_3$ and $R_4$ are as hereinbefore defined and the hydroxy group is trans to the bromo atom, with a base, such as potassium hydroxide, in a solvent, such as ether or aqueous dioxan.

Compounds of formula (VIII) are known and may be prepared in accordance with any appropriate known process, for example, by the process described in the aformentioned U.S. patents and European patent publications. Schematically, such process can be depicted thus.

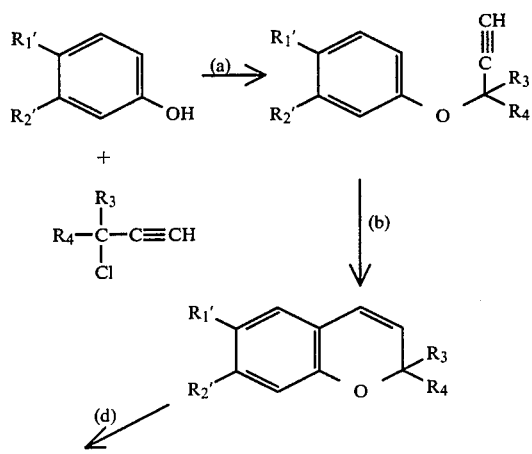

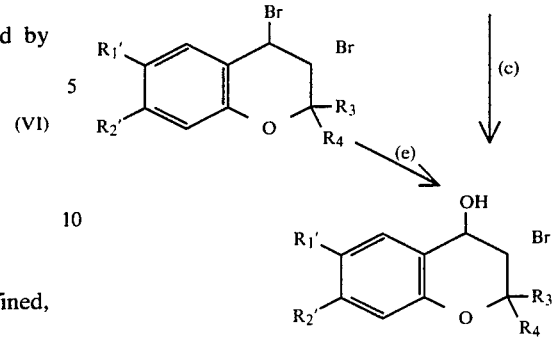

(a) Room temperature; NaOH/40% benzyltrimethylammonium hydroxide in methanol;
(b) Heat in o-dichlorobenzene;
(c) N-bromosuccinimide/dimethylsulphoxide/water;
(d) Bromine in carbon tetrachloride; and
(e) Acetone/water.

The above process may produce mixtures of compounds during reaction (b) owing to the two sites available for ring formation. It is therefore advisable to remove any of the undesired compound by, for example, chromatography, before reaction (c) or (d).

As mentioned previously, the compounds of formula (I) exist in optically active forms, and the processes of the present invention produce mixtures of such forms. The individual isomers may be separated one from the other by chromatography using a chiral phase.

The compounds of formula (III) and (VII) are also known or can be prepared analogously to the preparation of known compounds.

A number of the compounds of formula (II) are known from the aforementioned U.S. Patents and European Patent publications. However, there is a novel class of compounds falling ithin formula (II) which are of formula (IX):

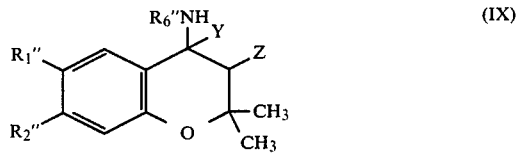
(IX)

wherein either one of $R_1''$ and $R_2''$ is hydrogen and the other is $C_{1-6}$ alkylcarbonyl, $C_{1-6}$ alkoxycarbonyl, $C_{1-6}$ alkylcarbonyloxy, $C_{1-6}$ alkylhydroxymethyl or cyanoor one of $R_1''$ and $R_2''$ is $C_{1-6}$ alkylcarbonyl, nitro or cyano and the other is amino and $R_8''$ is methyl or ethyl.

A preferred sub-class of compounds of formula (IX) are those wherein the alkyl groups or alkyl moieties of alkyl-containing groups are methyl or ethyl.

The compounds of formula (IX) are particularly useful intermediates, which can be prepared as hereinbefore described and which represent part of the present invention.

As mentioned previously, the compounds of formula (I) have been found to have blood-pressure lowering activity. They are therefore useful in the treatment of hypertension.

The present invention accordingly provides a pharmaceutical composition which comprises a compound of the formula (I) or a pharmaceutically acceptable salt thereof and a pharmaceutically acceptable carrier. In particular, the present invention provides an anti-hypertensive pharmaceutical composition which comprises an anti-hypertensive effective amount of a compound of the formula (I) and a pharmaceutically acceptable carrier.

The compositions are preferably adapted for oral administration. However, they may be adapted for other modes of administration, for example parenteral administration for patients suffering from heart failure.

In order to obtain consistency of administration it is preferred that a composition of the invention is in the form of a unit-dose. Suitable unit dose forms include tablets, capsules and powders in sachets or vials. Such unit dose forms may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

The compositions of the invention may be formulated with conventional excipients, such as a filler, a disintegrating agent, a binder, a lubricant, a flavouring agent and the like. They are formulated in conventional manner, for example in a manner similar to that used for known anti-hypertensive agents, diuretics and β-blocking agents.

The present invention further provides a compound of the formula (I) for use in the treatment of hypertension.

The present invention yet further provides a method of treating hypertension in mammals including man, which comprises administering to the suffering mammal an anti-hypertensive effective amount of a compound of formula (I) or a pharmaceutically acceptable salt thereof or a pharmaceutical composition of the invention.

The following descriptions relate to the preparation of intermediates and the following example relates to the preparation of a compound of formula (I).

Description 1

Trans-4-N-acetylamino-6-cyano-3,4-dihydro-2,2-dimethyl-2H-benzo[b]pyran-3-ol

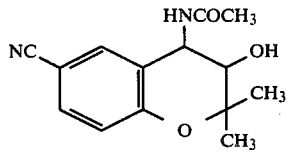
(D1)

6-Cyano-3,4-dihydro-2,2-dimethyl-3,4-epoxy-2H-benzo[b]pyran (10.0 g) was stirred in ethanol (20 ml) and the ammonium hydroxide solution (50 ml) for 4 days at room temperature. Evaporation gave a yellow gum (10.1 g) which solidified on standing.

This solid (1.0 g), anhydrous sodium acetate (2.00 g) and acetic anhydride (20 ml) were stirred for 5 hours at room temperature. The mixture was poured into water and extracted with ethyl acetate. This was washed with water and brine, and dried over MgSO2. Removal of drying agent, and evaporation gave a solid which was chromatographed using a chromaton (2 mm silica gel HF25 plate, solvent flow 6 ml/min elution with ethyl acetate-pentane using a gradient technique gave a fraction which contained the crude title compound. Recrystallisation of this material from ethyl acetate gave trans-4-N-acetylamino-6-cyano-3,4-dihydro-2,2-dimethyl-2H-benzo[b]pyran-3-ol (208 mgm) as crystals of m.p. 203-250.

NMR (CDCl3-DMSOd6) 1.25 (3H,s), 1.47 (3H, s), 2.08 (3H, s), 3.60 (q, J=9, 5 Hz), 4.93 (q, J=9, 8 Hz), 5.24 (d, J=5 Hz), 6.86 (d, J=8 Hz), 7.43 (q, J=8, 2 Hz) overlapping 7.50 (d, J=2 Hz) 8.00 (d, J=8 Hz).

Anal. $C_{14}H_{16}H_2O_3$ requires: C, 64.60; H, 6.20; N, 10.76. found: C, 64.51; H, 6.21; N, 10.78%.

Description 2

4-Acetylamino-6-cyano-2,2-dimethyl-2H-benzo[b]pyran

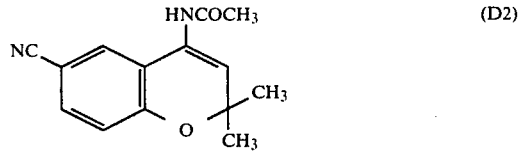
(D2)

The compound of example 2, (0.5 g) and sodium hydride (0.058 g, 80% dispersion in oil) were heated under reflux in dry xylene (50 ml) in an atmosphere of nitrogen for 48 hours. After cooling, water (25 ml) was added cautiously, and the layers separated. The organic phase was washed with water and brine, and dried over anhydrous magnesium sulphate. Filtration and evaporation gave a gum which was chromatographed (chromatotron, gradient elution: ethyl acetate-pentane, 2 mm silica gel, 6 ml/min) to give the title compound (230 mg) in the initial fractions, as needles (65 mg) from diethyl ether, having a m.p. of 146°-147° C.

NMR (CDCl3) 1.50 (6H, s); 2.23 (3H, s); 6.37 (1H, s); 6.90 (1H, d, J=9 Hz) overlapping 7.00 (1H, m); 7.45 (1H, q, J−9, 2 Hz) overlapping; 7.52 (1H, d, J=2 Hz).

EXAMPLE 1

4-Acetylamino-6-cyano-2,2-dimethyl-2H-1-benzopyran (compound 1)

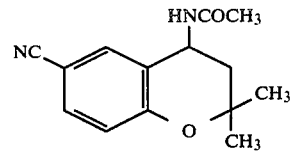

4-Acetylamino-6-cyano-2,2-dimethyl-2H-1-benzopyran (180 mgm) and 10% Palladium/carbon (100 mg) in ethanol (25 ml) were shaken under hydrogen for 6 days at room temperature. Filtration and evaporation gave a brown gum (180 mgm) which was purified using a chromatotron, elution with ascending concentrations of ethyl acetate in pentane, giving a fraction which was recrystallised from ethyl acetate-hexane to give the title compound (25 mgm) of m.p. 166°-167° C.

Mass spectrum $C_{14}H_{16}N_2O_2$ requires M+ at m/z 244.1212; found M+ at m/z 244.1216.

NMR (CDCl3) δ 1.33 (3H, s); 1.46 (3H, s); 1.72 (1H, t, J=8, 8 Hz); 2.08 (3H, s); 2.19 (1H, q, J=8, 4 Hz); 5.27 (1H, m); 6.05 (1H, d, J=5 Hz); 6.82 (1H, d, J=11 Hz); 7.37 (1H, q, J-11, 2 Hz); 7.53 (1H, narrow m).

The following compounds are prepared analogously and from intermediates described in EP No. 95316 and allowed U.S. patent application No. 496,174:

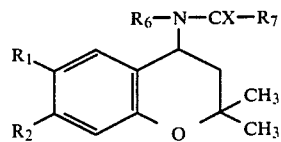

| Ex No | $R_1$ | $R_2$ | $R_6$ | $R_7$ | X |
|---|---|---|---|---|---|
| 2 | NC | H | $C_2H_5$ | $CH_3$ | O |
| 3 | NC | H | H | $CH=CH_2$ | O |
| 4 | NC | H | $CH_3$ | $CH_3$ | O |
| 5 | NC | H | H | $C_2H_2$ | O |
| 6 | NC | H | H | $(CH_2)_3CH_3$ | O |
| 7 | Cl | H | H | $CH_3$ | O |
| 8 | $CH_3CO$ | H | H | $CH_3$ | O |
| 9 | $CH_3CONH$ | $O_2N$ | H | $CH_3$ | O |
| 10 | $O_2N$ | $CH_3CONH$ | H | $CH_3$ | O |
| 11 | NC | H | H | $CH_2Cl$ | O |
| 12 | NC | H | H | $CH_2COCH_3$ | O |
| 13 | NC | H | H | $CH_3$ | S |
| 14 | NC | H | H | H | O |

Pharmacological Data

Systolic blood pressures were recorded by a modification of the tail cuff method described by I. M. Claxton, M. G. Palfreyman, R. H. Poyser, R. L. Whiting, European Journal of Pharmacology, 37, 179 (1976). A W+W BP recorder, model 8005, was used to display pulses prior to all measurements rats were placed in a heated environment (33.5°±0.5° C.) before transfer to a restraining cage. Each determination of blood pressure was the mean of at least 6 readings. Spontaneously hypertensive rats (ages 12–18 weeks) with systolic blood pressures >170 mmHg were considered hypertensive.

| Compound of Example | Time Post Dose Hours | % Change in Systolic Blood Blood | % Change in Heart Rate |
|---|---|---|---|
| 6 rats | 1 | −34 ± 6 | 2 ± 2 |
| Dose 1 mg/kg p.o. | 2* | −31 ± 8 | 0 ± 3 |
| Initial Blood | 4 | −38 ± 4 | 4 ± 2 |
| Pressure | 6 | −44 ± 7 | −1 ± 2 |
| 202 ± 6 mmHg | | | |
| Initial Heart Rate | 24 | −8 ± 4 | −6 ± 3 |
| 501 ± 10 beats/min | | | |

*At 2 hours 2 rats had no measurable pulse

Toxicity

No toxic effects were observed in the above test.

I claim:

1. A compound of the formula (I):

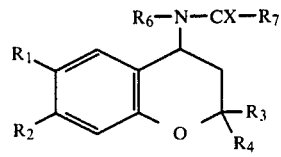

wherein:
$R_1$ is nitro, cyano, chloro, or acetyl and $R_2$ is hydrogen, or one of $R_1$ and $R_2$ is nitro, cyano or acetyl and the other is amino, methylamino, dimethylamino or acetylamino;
$R_3$ and $R_4$ are both methyl;
$R_6$ is hydrogen or $C_{1-6}$ alkyl;
$R_7$ is hydrogen or $C_{1-6}$ alkyl optionally substituted by hydroxy, $C_{1-6}$ alkoxy, $C_{1-6}$ alkoxycarbonyl or carboxy, or $C_{1-2}$ alkyl substituted by halogen, or $C_{2-6}$ alkenyl;
X is oxygen or sulphur; or when one or the other of $R_1$ and $R_2$ is an amino or an amino-containing group, a pharmaceutically acceptable salt thereof.

2. A compound according to claim 1 wherein $R_2$ is hydrogen and $R_1$ is acetyl, nitro or cyano.

3. A compound according to claim 2 wherein $R_2$ is hydrogen and $R_1$ is nitro or cyano.

4. A compound according to claim 1, wherein $R_6$ is hydrogen.

5. A compound according to claim 1, wherein $R_7$ is methyl.

6. 4-Acetylamino-6-cyano-2,2-dimethyl-2H-1-benzopyran.

7. A pharmaceutical composition for the treatment of hypertension, comprising an effective amount of a compound according to claim 1 or a pharmaceutically acceptable salt thereof and a pharmaceutically acceptable carrier.

8. The composition according to claim 7, wherein said compound is 4-acetylamino-6-cyano-2,2-dimethy-2H-1-benzopyran.

9. A method of treating hypertension in mammals including man, which comprises administering to the sufferer an anti-hypertensive amount of the compound according to claim 1 or a pharmaceutically acceptable salt thereof.

10. The method according to claim 9, wherein said compound is 4-acetylamino-6-cyano-2,2-dimethyl-2H-1-benzopyran.

* * * * *